(12) United States Patent
Ahola et al.

(10) Patent No.: US 6,991,802 B1
(45) Date of Patent: Jan. 31, 2006

(54) MULTILAYERED MATERIAL BEARING A BIOLOGICALLY ACTIVE AGENT AND THE PREPARATION THEREOF

(75) Inventors: Manja Ahola, Turku (FI); Risto Penttinen, Turku (FI); Anders Södergård, Turku (FI); Antti Yli-Urpo, Littoinen (FI)

(73) Assignee: DelSiTech Oy, Turku (FI)

( * ) Notice: Subject to any disclaimer, the term of this patent is extended or adjusted under 35 U.S.C. 154(b) by 549 days.

(21) Appl. No.: 10/069,785

(22) PCT Filed: Aug. 29, 2000

(86) PCT No.: PCT/FI00/00730

§ 371 (c)(1),
(2), (4) Date: May 8, 2002

(87) PCT Pub. No.: WO01/15751

PCT Pub. Date: Mar. 8, 2001

(30) Foreign Application Priority Data

Sep. 1, 1999 (FI) .................................. 19991852

(51) Int. Cl.
*A61F 2/02* (2006.01)
*A61K 9/14* (2006.01)

(52) U.S. Cl. ...................... 424/423; 424/400; 424/422; 424/484

(58) Field of Classification Search ................ 424/400, 424/422, 423, 484
See application file for complete search history.

(56) References Cited

U.S. PATENT DOCUMENTS

| 4,588,624 | A |   | 5/1986 | Nygren et al. ................ 428/36 |
|---|---|---|---|---|
| 5,001,062 | A |   | 3/1991 | Larsson et al. ............. 435/176 |
| 5,100,668 | A |   | 3/1992 | Edelmann et al. .......... 424/422 |
| 5,820,917 | A | * | 10/1998 | Tuch .......................... 427/2.1 |
| 5,830,480 | A | * | 11/1998 | Ducheyne et al. .......... 424/400 |
| 5,876,433 | A |   | 3/1999 | Lunn .............................. 623/1 |
| 6,013,855 | A | * | 1/2000 | McPherson et al. ..... 623/23.76 |

FOREIGN PATENT DOCUMENTS

| EP | 0 305 346 A1 | 3/1989 |
|---|---|---|
| EP | 0 305 346 B1 | 3/1992 |
| EP | 0 604 022 | 6/1994 |
| EP | 0 832 655 A3 | 4/1998 |
| EP | 0 923 953 | 6/1999 |
| EP | 0 809 999 A3 | 11/1999 |
| FI | 79 027 | 7/1989 |
| FI | 885 496 | 11/1989 |
| FI | 93 610 | 1/1995 |
| WO | 96/02259 | 2/1996 |

* cited by examiner

Primary Examiner—Carlos A. Azpuru
(74) Attorney, Agent, or Firm—James C. Lydon

(57) ABSTRACT

A material for medical use in humans and/or animals bearing a biologically active agent, the material being multilayered, as well as a device of this material and a method to produce it. The material includes a core material, where the core material is formed into a body, optionally having the shape of a finished device; two or more layers of coating material of which the first layer has been applied onto the core material and additional layers have been applied onto the coating material of a preceding layer; and where at least one of the layers includes the biologically active agent. A feature of this invention is that the coating material is a biopolymer, a sol-gel produced silica gel or a biologically active molecule.

15 Claims, 2 Drawing Sheets

6,991,802 B1

MULTILAYERED MATERIAL BEARING A BIOLOGICALLY ACTIVE AGENT AND THE PREPARATION THEREOF

This application is a U.S. national stage of International Application PCT/FI00/00730, filed Aug. 29, 2000 and published on Mar. 8, 2001 in the English language.

This invention relates to a novel multilayered material for medical use in humans and animals, in the form of a shaped body, that can optionally have an anatomic and/or physiologic function, said multilayered material bearing biologically active agents. Furthermore, the invention concerns multilayered materials shaped into a body, into which such biologically active agents can be introduced. Still further, the invention concerns a method for preparing the novel multilayered material bearing biologically active agents.

BACKGROUND

Medical use of multilayered materials has been disclosed e.g. to provide sustained release or controlled release of oral or transdermal drugs (e.g. U.S. Pat. Nos. 4,451,260, 5,093,200, 5,645,858, 5,662,935, 5,681,583 and 5,332,577), or synthetic skin etc. (e.g. U.S. Pat. Nos. 4,060,081, 5,658,582 and 5,876,742).

Biodegradable polymers (Pitt et al. 1979, Ye and Chien 1996) as well as sol-gel processed silica xerogels (Kortesuo et al. 1999) have been used in controlled drug delivery devices, but their composites have not been used in these applications. Bioactive glass has been utilized in many orthopedic applications (Heikkilä et al. 1995). It is known that bioactive glass promotes bone formation.

It has not been possible to build up devices with elegant drug delivery properties with disclosed methods and materials. The novel combination of e.g. the above mentioned biodegradable materials in multilayered materials makes it possible e.g. to alter delivery properties by using different coating and/or core materials. Multilayered materials enable the incorporation of biologically active agents into bioactive glass. This has been possible only by adsorption, which process is difficult to control.

OBJECTS OF THE INVENTION

One object of this invention is to provide medical devices made of a material tailored to be used in the human or animal body that is multilayered wherein desired regions and/or layers, i.e. coatings, of the device are provided with one or more agents having a desired biological activity.

Another object is to achieve a medical device having coatings into which a therapeutically active agent is loaded, and from which said therapeutically active agent is released at a controlled rate.

SUMMARY OF THE INVENTION

Thus, according to one aspect, this invention concerns a material for medical use in humans and/or animals bearing a biologically active agent, said material being multilayered comprising
 a) a core material, wherein said core material is formed into a body, optionally into a body having the shape of a finished device,
 b) two or more layers of coating material of which the first layer has been applied onto said core material and additional layers have been applied onto said coating material of a preceding layer and
 c) said biologically active agent incorporated in at least one of the coating layers.

The coating material is a biopolymer, a sol-gel produced silica gel or a biologically active molecule.

According to another aspect, this invention concerns a device made of a material, useful for finishing into a device of a material for medical use in humans and/or animals bearing a biologically active agent, wherein said material is multilayered and formed into a body of the shape of a finished device comprising
 a) a core material, wherein said core material is formed into a body, optionally into a body having the shape of a finished device,
 b) two or more layers of coating material of which the first layer has been applied onto said core material and additional layers have been applied onto said coating material of a preceding layer and
 c) said biologically active agent incorporated in at least one of the coating layers.

The coating material is a biopolymer, a sol-gel produced silica gel or a biologically active molecule.

According to a further aspect, this invention concerns a method for the preparation of a multilayered material for medical use in humans and/or animals bearing a biologically active agent, said material comprising
 a) a core material, wherein said core material is formed into a body, optionally into a body having the shape of a finished device,
 b) two or more layers of coating material of which the first layer has been applied onto said core material and additional layers have been applied onto said coating material of a preceding layer and
 c) said biologically active agent incorporated in at least one of the coating layers, and wherein said coating material is a biopolymer, a sol-gel produced silica gel or a biologically active molecule. The method comprises the repeated steps of
 i) coating said core material or a coating material of a preceding layer with a coating material which optionally can comprise a biologically active agent and
 ii) optionally binding a biologically active agent to the said coating.

DETAILED DESCRIPTION OF THE INVENTION

Figure 1:
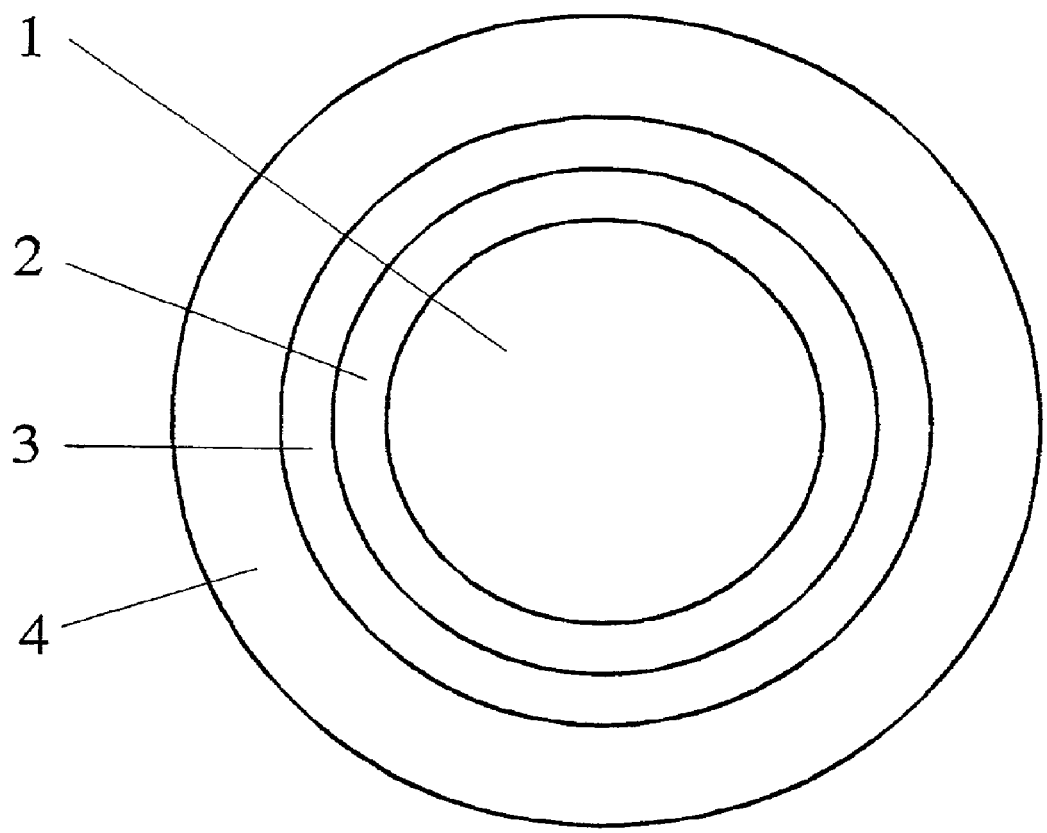
FIG. 1 shows a schematic cross-sectional view of a rod of multilayered material.

According to invention the multilayered material bearing the biologically active agent has been shaped to a device. Said device comprises a core material formed into a body, optionally into a body having the shape of a finished device, wherein the biologically active agent is bound to the core material or to a coating material. Said core material and the coating materials of the different layers can be the same or different and said biologically active agents comprised in, or bound to said core material or said coating material can as well be the same or different.

Definitions and Preferred Embodiments

The term "biologically active agent" shall be understood as an agent causing a valuable effect in vivo, such as a bioactive effect (i.e. promoting the binding of bone to an artificial implant inserted into the mammal body), a therapeutic effect, or the like.

It shall be noted that certain biologically active agents also possess the ability to bind other biologically active agents. As an example can be mentioned silica gel, which as such may or may not, depending on e.g. its dissolution rate, nanoporosity and specific area, be biologically active (i.e. bioactive) in that it promotes tissue maintenance or formation. Furthermore, silica gel can be used as a matrix which can be loaded with a biologically active agent (e.g. a drug), which then is released in certain conditions, e.g. in body fluids. Silica gel can therefore be used for the controlled release of therapeutically active agents. Analogously polymers can act as vehicles used to release biologically active molecules. The function of polymers can be modified by molecular size and derivatization.

As particularly useful biologically active agents in implantable devices can be mentioned non-toxic inorganic molecules or polymers thereof; a silica gel as such or a silica gel loaded with a therapeutically active agent.

The biologically active agent can be any organic, inorganic or living agent that is biologically active. The biologically active agent can be a protein, a polypeptide, a polysaccharide (e.g. heparin), an oligosaccharide, a mono- or disaccharide, an organic compound, an organometallic compound or an inorganic compound containing any element with an atomic number ranging from 3 to 84. It can be a living or dead cell, bacterium, a virus or a part thereof. It can be a biologically active molecule such as a hormone, a growth factor, a growth factor producing virus, a growth factor inhibitor, a growth factor receptor, an integrin blocker (e.g. a IIa/IIIb inhibitor) or a complete or partial functional gene in sense or antisense orientation in a suitable expression vector or in any other expression vector construct for local delivery of therapeutically active agents. Biologically active agents include those especially useful for long-term therapy, such as hormonal treatment, for example contraception and hormone replacement therapy, and for treatment of diseases such as osteoporosis, cancer, epilepsy, Parkinson's disease and pain. The suitable biologically active agents may be, e.g. anti-inflammatory agents, anti-infective (e.g. antibiotics and antiviral agents), analgesics and analgesic combinations, antiasthmatic agents, anticonvulsants, antidepressants, antidiabetic agents, antineoplastics, anticancer agents, antipsychotics, agents used for cardiovascular diseases. The multilayered material can be tailored to release the biologically active agent or agents composed in it at a controlled rate in in vivo conditions.

The word "body" shall be understood to be any defined piece or continuous article such as a granule, spherulite, sheet, film, plate, stick, pin, screw, tube, fiber, hollow fiber, woven fabric or non-woven fabric, or the like also when built to resemble human or animal body parts such as ear, nose, joints, filler in plastic form, etc. or parts thereof.

The term "biopolymer" shall be understood to mean either polymers based on renewable raw materials, biodegradable or not, e.g. cellulose, or synthetic polymers which are biodegradable, e.g. polylactides.

According to a preferred embodiment, the multilayered material bears more than one biologically active agent. The different biologically active agents can be composed in the same or different coating layers or in the core material.

According to another preferred embodiment each biologically active agent can be incorporated in the core material and/or a preferred coating layer or preferred layers. Further the biologically active agent can be designed to be composed in a desired region of the core or any coating layer of the body.

According to yet another preferred embodiment of this invention, the multilayered material is formed to a device to be implanted into the human or animal body to serve different clinical applications, [e.g. stents, implants (dental or orthopedic), implants for controlled drug delivery, bone fixation pins, fixation plates, fixation bolts, regeneration matrixes, etc.]. The biologically active agents must of course be pharmaceutically acceptable.

According to a particularly valuable embodiment, the multilayered material is formed to a stent. A stent is a splint or tube to be placed temporarily or permanently inside a duct, canal or blood vessel to aid healing or relive an obstruction. Stents are inserted in blood vessels, e.g. in balloon angioplasty, where the balloon is placed inside an expandable stent (tube) which is expanded as the balloon is pressurized. Known stents are typically tubes of metallic networks.

The stent according to this invention can be made of a biodegradable multilayered material or for example so that only the core and/or specific layers of said material are of a biodegradable material whereas the rest of the stent is of inert material. It can, moreover, be of a biodegradable bioactive glass fiber or of a sol-gel produced silica gel fiber. The fiber is formed by multilayer coating according to this invention. Selected layers e.g. the inner wall of the tube can be coated with a silica gel loaded with a biologically active agent e.g. the anticoagulant drug heparin. The silica gel can e.g. be strongly bound to the inner wall of the tube via cleaved alkoxysilyl substituents on grafted monomers. A silica gel coating made in this manner is stable and also thin, which is an important feature in this field of use. The outer wall of the tube can, if desired, be provided with other biologically active agents.

According to a particularly valuable embodiment the core of the multilayered system can be either a biodegradable silica body, e.g. bioactive glass or sol-gel produced silica gel, or a biopolymer, which can be either biodegradable, e.g. polylactide, or inert, e.g. cellulose.

In the embodiment shown in FIG. 1 the core material 1 is bioactive glass or sol-gel produced silica gel coated with the following layers: a biodegradable polymer layer 2, a sol-gel produced silica gel or a biologically active molecule (e.g. heparin) layer 3 and another biodegradable polymer layer 4 of the same or a different polymer from the previous polymer layer 2. This arrangement, enables directed, targeted delivery of biologically active agents. The biologically active agents can be composed in both the sol-gel produced body (see example 1) or coating layer and the polymer body or coating layer (see example 2). The attachment of different layers can be improved by using different surface modification techniques, e.g. radiation induced grafting (example 2) or silylation treatment (example 3). All layers can have a different biologically active agent, if necessary. The thickness of the layers, e.g. layers 2, 3 and 4 in FIG. 1, can be varied widely, e.g. from about 100 nm to 1 mm depending on specific needs.

Figure 2:
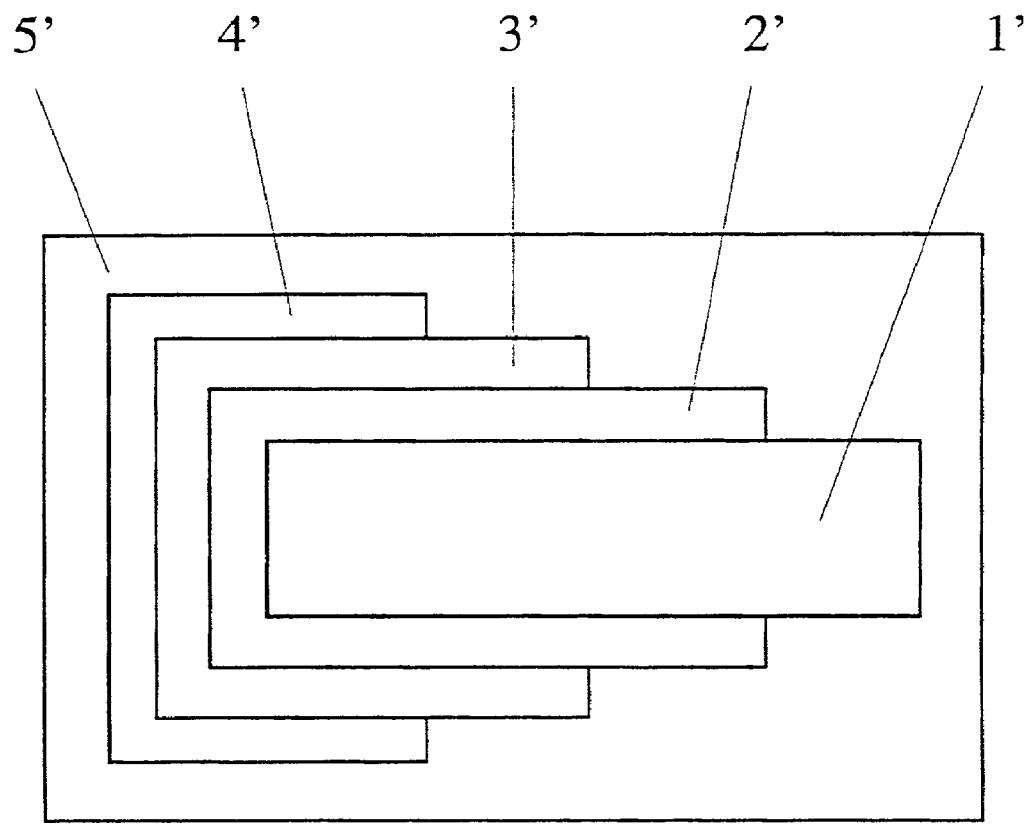
FIG. 2 shows a schematic cross-sectional view of a capsule of a multilayered material.

The embodiment shown schematically in FIG. 2 exemplifies that cumulative layers 2', 3', 4', 5' applied on the core material 1' can be tailored so as to cover only specific parts of the embodiment, in this case a capsule, but could be any device e.g. to be implanted into the human or animal body. Thus it is possible to tailor specific embodiments for specific purposes. The different layers at different locations can serve different purposes. For example capsules to be taken orally, capsules thus passing through the intestine, can be activated and/or dissolved by different pH and digestive enzymes at different locations of the intestine and activation and/or dissolution rate can be influenced by the chemical composition and area of each specific layer. Alternatively devices to be implanted can comprise asymmetrical layers with different compositions affecting different directions differently and/or layers releasing their biologically active agents at different stages of the lifecycle of the device e.g. triggered by a change in pH caused e.g. by a gradual decrease of an initial inflammation at the location of the implant.

A medical device manufactured according to this invention can be used for drug delivery. The degradation of the drug containing implant may or may not be a pH dependent process. The invention can be used to obtain targeted drug delivery. Functional devices that deliver drugs can be made by choice of core and coating material to disappear or not to disappear from the body. A medical device according to this invention can be used as a bone graft substitute to enhance the rate and probability of fracture healing by delivering antibiotics either alone or in addition to growth factors. In fractures involving, for example, the spine, the incorporation of anti-inflammatory agents and analgesics will help to control inflammation, which might delay the healing process, and thus contribute to patient comfort during the healing process.

Local drug release after cancer surgery using a medical device according to this invention could provide targeted and long-lasting disease control.

Inducing the growth of blood vessels in bioartificial tissues (angiogenesis) could be stimulated by coating a medical device according to this invention with growth factors or growth factor producing viruses, which growth factors trigger blood vessel formation.

A woven or nonwoven mat made of fibers according to this invention containing one or more biologically active agents can be used for a temporary skin substitute or for guided tissue regeneration.

A multilayered body according to this invention can be designed into a pharmaceutical for oral use optionally comprising multiple drugs Multiple layers of specific materials could be used to e.g. achieve slow release of the drug or drugs and/or it could be used to e.g. ensure controlled release of the drug or drugs in e.g. a part of the digestive system, which is optimal for the uptake of each specific drug.

The main field of this invention can briefly be summarized as utilization of novel multilayered materials equipped with a biologically active agent which give raise to a desired respond when brought into contact with living tissues giving said materials tailored properties for medical use in humans and animals.

The invention is disclosed in more detail by the following experiments.

EXPERIMENTAL SECTION

Example 1

Application of Heparin Loaded Silica Gel Onto a Grafted PLLA-co-CL Copolymer

In this example, heparin is immobilized onto silica gel and then grafted PLLA (poly-L-lactide) sheets are coated with the heparinized silica-gel. Bulk heparinized silica-gel samples were obtained for the drug delivery ability tests. It is known that silica-gel can be used as a drug delivery system (Kortesuo et al. 1999).

Preparation of Silica-Sol

The heparin immobilized silica-sol was prepared by a two step sol-gel process using acid as a catalyst (Brinker and Scherer 1990, Ellerby et al. 1992). The following reagents were used: tetraethoxysilane (TEOS) (Aldrich), deionized water, ethanol nitric acid ($HNO_3$) (Merck) and ammonium hydroxide ($NH_4OH$). The r-value (water/TEOS molar ratio) was 3.55. Ethanol was used as a solvent to obtain better viscosity (water/ethanol molar ratio=1). $NH_4OH$ was used to raise pH up to 4.5. Heparin used was a sodium salt of heparin obtained from Orion Corporation (biological activity 139 I.U./mg). To obtain 100 ml hydrolysis solution, 48 g of tetraethoxysilane (TEOS), 45 g of deionized water, 4 g of glycerol and 10.1 g of catalyst (0.04 M $HNO_3$) were added to a glass container and stirred until the inorganic water phase and the organic TEOS phase had become homogenized.

To obtain small bulk pieces for the drug delivery test, the hydrolysis solution was divided into smaller samples (V=0.5 ml) that were aged in sealed polystyrene container at 40° C. and 40% relative humidity for 3 days. After this gelation process samples were dried at room temperature for an additional 3 days. The heparin content in one gel piece varied from one to 15 weight-% (calculated from the dry weight). The $H_2O$/TEOS-moleratio (r-value) was between 14 and 16, and pH was 4.5. The same sol was used when the grafted polymers were coated.

The coating was applied to Poly(L-lactide)-co-ε-caprolactone (PLLA-co-CL) sheets immediately after hydrolysis by dipping technique. The uniformity of coating was examined with scanning electron microscopy (SEM) measurements.

Functionalization of the Polymer

PLLA and PCL (polycaprolactone) were polymerized according to a method described by Holmlund (Holmlund 1999). The pre-weighed polymer samples were irradiated by using an Electrocurtain® electron accelerator in air at an acceleration voltage of 175 kV (Södergård 1998 a and b). The irradiated films were removed from the accelerator and immersed into the monomer solutions at ambient temperature for various reaction times without using any homopolymerization inhibitor.

| Polymer: | Poly(L-lactide)-co-ε-caprolactone (PLLA-co-CL) |
|---|---|
| Monomer: | Acrylamide (Promega) |
| Extent of grafting: | About 20% |
| Monomer distribution: | As a uniform coating |

The extent of grafting was gravimetrically determined from the following equation:

$$E(\%) = 100 \cdot \frac{m_1 - m_0}{m_0}$$

where $m_0$ and $m_1$ are the weights of the ungrafted and the grafted sample, respectively.

The monomer solutions were purged with nitrogen for at least 30 minutes before the grafting in order to minimize the presence of oxygen during the grafting process. The grafted films were washed with ion-exchanged water for several hours in order to remove homopolymer, and dried to constant weight in vacuum at room temperature.

Tests

The following functional tests were performed: the biocompatibility of the materials was examined by using cultured cells, the release of heparin and silica were studied by dissolution testing, and the biological activity of the bound and released heparin was determined by a thrombin assay (Kang et al. 1997). From the dissolution test heparin was determined by a toluidine blue test (Smith et al. 1980 and Park et al. 1991) and silica by a spectroscopic method (Koch and Koch-Dedic 1974). Scanning electron microscopy (SEM) was used to study the morphological characteristics of the silica-gel coating. Materials were in vitro tested by culturing cells on materials and by measuring cytotoxicity of materials.

Dissolution Test

SBF was prepared by dissolving NaCl, $NaHCO_3$, KCl, $K_2HPO_4 \times 3H_2O$, $MgCl_2 \times 6H_2O$, $CaCl_2$, $Na_2SO_4$, TRIZMA® HCl and TRIZMA® base as shown in Table 1. The fluid was adjusted at physiological pH 7.40 and temperature 37° C. The composition of inorganic ions emulated that of human blood plasma.

TABLE 1

Reagents used for the SBF solution.

| Reagent | Amount/1 $dm^3$ ($H_2O$) | Manufacture/purity |
|---|---|---|
| NaCl | 7.9951 | Riedel-deHaën, pro analysis/99.8% |
| $NaHCO_3$ | 0.3534 | Merck, pro analysis/99.5% |
| KCl | 0.2243 | Merck, pro analysis/99.5% |
| $K_2HPO_4 \cdot 3H_2O$ | 0.2281 | Merck, pro analysis/99% |
| $MgCl_2 \cdot 6H_2O$ | 0.3053 | Merck, pro analysis/99% |
| $CaCl_2$ | 0.2776 | Merck, pro analysis/99% |
| $Na_2SO_4$ | 0.0709 | Merck, pro analysis/99% |
| TRIZMA HCl * | 6.2414 | Sigma Ultra/99.9% |
| TRIZMA base ** | 1.2591 | Sigma Ultra/99.9% |

* TRIZMA ® HCl: tris[hydroxymethyl]aminomethane hydrochloride $(HOCH_2)_3CNH_2 \cdot HCl$
** TRIZMA ® base: tris[hydroxymethyl]aminomethane $(HOCH_2)_3CNH_2$ From 20 to 25 mg of heparinized silica gel was immersed in 50 ml SBF in a polyethylene bottle covered with a tight lid. Two parallel samples and six different time points were used. All bottles were placed in a shaking water bath at 37° C. All samples were filtered before the ion concentration (Si) analysis was carried out by spectroscopic method described by Boltz and Mellon 1947.

Cell Growth and Cytotoxicity Testing

The following materials were tested: copolymer as such, PLLA, CL, copolymer grafted in both ways and bulk heparinized silica gel. The materials were in vitro tested by culturing cells on materials and by measuring cytotoxicity of materials. The purpose of this was to evaluate whether the grafting process and grafted materials are safe for living tissues, and also to choose the best candidates for in vivo testing. Human gingival fibroblasts (Häkkinen 1995) were routinely cultured in Dulbecco's Modification of Eagle's Medium (DMEM), including 10% (v/v) Foetal Calf Serum (FCS, kibbutz Beit Haemek, Israel), 4,500 mg/l glucose, 3.7 g/l $NaHCO_3$ and penicillin-streptomycin solution (Gibco-BRL, 10,000 U/mil and 10,000 µg/ml in saline) 1 ml/l. Cells were cultured on petridishes (Ø 10 cm) at +37° C. and 5% $CO_2$ atmosphere. The medium was changed every other day and the cells were harvested at confluency. Only cells from nearly confluent dishes were used for experiments.

Materials used for cell culturing were washed with 20% ethanol and sterile deionized water. Then they were attached to culture dishes with silicone grease. Amount of cells per sample material was about ⅙ of the confluent petridish. Medium was changed every other day and cell growth was followed and investigated with a microscope.

Cytotoxicity of materials was evaluated using a modification of the lactate dehydrogenase (LDH) method (Korzeniewski and Callewaert 1983). Materials were tested as extracts. Standard 6-well plates (Nunc) were used. One confluent petridish (Ø 10 cm) was used per test. Cells were first washed with 4 ml of EDTA solution [in phosphate buffer solution (PBS), pH 7.4] and then incubated 5 minutes in 4 ml of trypsin EDTA solution (40/0.4) at +37° C. [Trypsin stock=2.5% (w/v) in normal saline, GibcoBRL]. Detached cells were transferred into a 15 ml centrifuge tube and centrifuged 5 minutes at 800 rpm. Finally cells were suspended in 5 ml of medium. From this suspension 200 µl per well was added. Cells were cultured in these plates as mentioned before using 2 ml medium per well, changing medium every other day until the cultures had reached confluency.

When all cultures had almost reached confluency, the test materials were extracted. Materials (ca. 0.5 $cm^2$) were dipped into 20% ethanol and rinsed with sterile deionized water. Then they were dipped into sterile eppendorf tubes and 1 ml of medium was added. These tubes were incubated for 24 hours at +37° C. After that the medium in the wells of the test plates was removed and dead cells detached with 0.02 weight-% EDTA solution. Then 1 ml of fresh medium was added into each well. The extracts were added, and into wells for spontaneous LDH release 1 ml of medium was added. For wells of maximal LDH release 200 µl of 10% Triton X-100 and 1 ml of medium was added. This test system was incubated in cell culture conditions (as mentioned before) for 24 hours.

After 24 hours a sample of 500 µl from each well was taken. LDH measurement was carried out at room temperature (20–25° C.). Solution A was prepared by pipetting 432 µl of 30 mM sodiumpyruvate (Sigma) in Tris-Cl buffer (TRIZMA®, Sigma), pH 7.4 and 432 µl of 6.6 mM NADH (FlukaChem) in the same buffer. The reagent was then diluted with 2550 µl of the same buffer. The ready made solution A was kept in dark between single measurements and vortexed carefully before use.

The samples were diluted by mixing 200 µl of the sample with 700 µl of Tris-buffer (same as above). They were vortexed and transferred into cuvettes. Measurements were carried out using a Shimadzu UV/Vis spectrophotometer at 340 nm wavelength. The reaction was started by adding 100 µl of solution A into the cuvette containing a sample, and the reaction was followed for 7 minutes. The slope was measured for the first 120 second period and used for indication of the amount of LDH released into the medium. Cytotoxicity (% D) was calculated by using the equation:

$$\% D = \left[\frac{(|A|-|B|)}{(|A|-|B|)}\right] \cdot 100\%$$

A=sample slope
B=spontaneous release well slope and
C=Triton X-100 well slope.

Results

Both the dissolution rate of the silica-gel and releasing rate of heparin was examined by using the bulk gel prepared by sol-gel technique. Up to 15%, calculated from the theoretical dry weight, of heparin was successfully immobilized to the silica-gel produced by an acid catalyzed hydrolysis reaction.

During the 24 days, 45% of heparin loaded was released. Each heparin concentration used, 1–15 mass-% calculated from the theoretical dry weight, had similar releasing profile. Heparin concentrations were studied by toluidine blue method (Smith et al. 1980 and Park et al. 1991). Heparin released retained its biological activity as an anticoagulant when examined by the HEPRN® method.

According to information obtained from SEM studies, a uniform silica-gel coating was obtained on a surface of the acrylamide grafted PLLA-co-CL sheet. The thickness of the coating produced was 0.3 mm and its cracking after bending was minimal.

When human gingival fibroblasts were grown under cell culture conditions on coverslips, without and together with small silica-gel particles, it was found that cell growth was not influenced by the presence of the gel. Cells divided and spread normally and finally covered the silica-gel particles even though they were topographically elevated from the substratum surface. From the results of the in vitro test it seems obvious that silica-gels do not have any toxic or other harmful effects on fibroblasts growing in contact with the material. The present results agree with previous results indicating that silica-gels are biocompatible materials and promising dissolvable vehicles for delivery of biologically active molecules. The gels have no harmful effects on living tissues as can also be seen from the results of in vivo testing (Ahola et al., 1997 and Kortesuo et al., 1999).

Example 2

Control of the Retention of a Biologically Active Molecule (Heparin) to a Polymer Carrier by Varying the Chemical Reactivity (Functionality) of the Carrier by Grafting.

In this example, the degradable polymer (PLLA) is coated with biologically active agents. The surface properties of the copolymers of poly-L-lactide (PLLA) (Neste Ltd.) and poly-ε-caprolactone (PCL) (Sigma Co.) (PLLA/PCL=50/50) were altered by grafting with acrylamide (Promega Co.) onto the surface of PLLA-co-CL by electron beam (EB) irradiation (Holmlund 1999). The grafted polymer sheets were washed thoroughly with ethanol and deionized water. The grafted surface was then able to attach silica-gel or biologically active molecules such as heparin.

The grafted polymer was allowed to react with heparin solution (0.025 mg heparin/5 ml incubation solution). Sodium salt of heparin was from Orion Pharma (biological activity 139 I.U./mg). pH of the solution was adjusted before heparin addition, by acetic acid buffer (pH 4.5) and TRIS- or phosphate buffer (pH 8). The polymer sheets were incubated with this heparin solution. The incubation times varied from 2 to 96 h and incubations were carried out at 25 or 37° C. Sheets with attached heparin were washed thoroughly with deionized water.

The silica-sol immobilized heparin was prepared by a two step sol-gel process using nitric acid as a catalyst (Ellerby et al. 1992). The following reagents were used, TEOS (Aldrich), deionized water, nitric acid ($HNO_3$) (Merck), ammonium hydroxide ($NH_4OH$) and heparin sodium salt (Orion, biological activity 139 I.U./mg). To obtain 100 ml hydrolysis solution 48 g of TEOS, 45 g of deionized water and 10.1 g of catalyst (0.04 M $HNO_3$) were added to a glass beaker and stirred until the ingredients formed a homogenous solution. The silica gel coating was applied by dipping grafted polymer sheets into the homogenous hydrolysis solution.

The following functional tests were performed: the biocompatibility of the materials was examined by using cultured cells, the release of heparin and silica were studied by dissolution test and biological activity of the bound and released heparin was determined by the thrombin assay (Kang et al. 1997). From the dissolution test heparin was studied by toluidine blue test (Smith et al. 1980 and Park et al. 1991) and silica by spectroscopic method (Koch and Koch-Dedic 1974). SEM was used to study the morphological characteristics of the silica gel coating.

Results and Discussion

The results from the cell culture tests, cytotoxicity test (Korzeniewski and Callewaert 1983), suggest that acrylamide grafting does not alter the biocompatibility of the PLLA-co-CL. Both contact and extract tests were carried out, and no significant differences between these results were observed.

Direct Immobilization of Heparin

Changing the reaction conditions, e.g. reaction time or temperature and pH of the incubation solution, could vary the amount of heparin immobilized on the grafted PLLA-co-CL. The attachment of heparin was best when acidic conditions (pH 4.5, acetic acid) were used (Table 1). Up to 98 $\mu g/cm^2$ of heparin was immobilized on the surface of the PLLA-co-CL graft polymer. The results were rather good even when only deionized water was utilized as a solvent. If the incubation solution is basic, the chemical structure of the buffering solution must be taken into account.

TRIS-buffer, which is a combined solution of TRIZMA HCl: tris[hydroxy-methyl]aminomethane hydrochloride $(HOCH_2)_3CNH_2 \times HCl$ (Sigma Ultra/99.9%) and TRIZMA base: tris[hydroxymethyl]aminomethane $(HOCH_2)_3CNH_2$ (Sigma Ultra/99.9%), should be avoid because TRIS may react with heparin preventing the attachment to the polymer. By using a phosphate buffer the attachment of heparin is possible, so the absence of heparin on the polymer when using TRIS is not a matter of pH alone. Overall, the attachment of heparin to the surface was better in acidic conditions than in basic.

TABLE 1

Effect of pH on the attachment of heparin on the surface of PLLA-co-CL polymer sheets. Size of the sheets used for the measurements was 0.25 $cm^2$

| pH | pH adjusting reagent | Heparin (mg) (toluidine test*) | Heparin ($\mu g$)/$cm^2$ |
|---|---|---|---|
| 4.5 | acetic acid buffer | 23 ± 5 | 94 |
| 5.7 | deionized water | 9 ± 2 | 36 |
| 8.0 | TRIS-buffer | — | — |
| 7.8 | phosphate buffer | 3 ± 1 | 10 |

*The result is a mean value of three parallel measurements.

According to the thrombin test, the immobilized heparin retains its biological activity against thrombin formation. At least 76% of heparin, observed on the surface by the toluidine blue test, showed biological activity as well. In the dissolution test, one week in simulated body fluid at 37° C., heparin was still immobilized since no heparin was released as estimated by the toluidine blue test or by the thrombin test.

Silica Gel Immobilized Heparin Coating

SEM pictures of the grafted surfaces showed that a uniform, about 0.3 μm thick, silica-gel coating was obtained with the dipping technique. Cracking of the silica-gel layer was minimal after bending sheets several times 90°. Heparin released from the silica coatings during the dissolution test retained its anticoagulant activity. The releasing rate of heparin follows that observed for silica, after one week half of the immobilized heparin was released.

Example 3

The Attachment of a Polymeric Layer on a Top of Bioactive Glass.

In this example, the degradable bioactive glass-13 (composition: 6% $Na_2O$, 12% $K_2O$, 5% MgO, 20% CaO, 4% $P_2O_5$ and 53% Si202) (Brink 1997) is coated with biocompatible, degradable polycaprolactone polymer by using organomodified silanes as coupling agents.

Silylation of Fibers

The biodegradable glass-13 fibers were prepared from glass melt (near 1100° C.) by drawing technique. After cooling down to room temperature the fibers were cut into small pieces (circa 10 cm long). These fibers were placed into a 50 ml falcon tube and the tube was filled with silylation reagent (2% of dichlorodimethylsilane ($C_2H_6Cl_2Si$) in trichloromethane ($CHCl_3$) solution). The silylation lasted for 10 min. Before washing the fibers carefully with deionized water, the silylation coating was let to stabilize for 24 h. The washed, silylated fibers were dried in a vacuum deccicator for an additional 24 h.

Polymer Coating of Fibers

The polycaprolactone (PCL) was dissolved in tetrahydrofurane (THF) (4,149 g of PCL in 100 ml of THF) and the silylated glass fibers were dipped into the solution. After dipping the fibers were dried at room temperature.

Results and Conclusion

The polymer coating layer formed on the glass fiber was uniform and the method explained above is an easy way to modify glass fibers.

REFERENCES

Ahola, M., Kortesuo, P., Karlsson, S., Kangasniemi, I., Kiesvaara, J., and Yliurpo, A., 23$^{rd}$ Annual Meeting of the Society for Biomaterials, Apr. 30–May 4, 1997, New Orleans, USA, *Book of Abstracts*, p. 364.

Boltz, D. F. and Mellon, M. G., *Anal. L Chem.*, 19 (1947) 873.

Brink, M., Thesis, Abo Akademi University, 1997.

Brinker, C. J., and Scherer, G. W., *Sol-Gel Science; The Physics and Chemistry of Sol-Gel Processing*, Chapter 5, Academic Press, Inc., San Diego, USA, 1990.

Ellerby, L. M., Nishida, C. R., Nishida, F., Yamanaka, S. T., Dunn, B., Valentine, J. S., Jeffrey, I. Z., *Science*, 28 (1992) 1113–1115.

Heikkilä, J. T., Mattila, K. T., Andersson, Ö. H., Yli-Urpo, A., and Aho, A. J., Behavior of bioactive glass in human bone, in Bioceramics 8. (Eds.) Hench L. L. and Wilson, J., Pergamon/Elsevier Science, Oxford, Great Britain, 1995, pp. 35–40.

HEPRN, Test methodology for the aca® discrete clinical analyzer, Du Pont Company, Wilmington, Del. 19898, USA.

Holmlund, P., *Diploma Thesis*, Abo Akademi University, Finland, 1999.

Kang, L. K., Kwon, O. H., Kim, M. K., Lee, Y. M., and Sung, Y. X., *Biomaterials*, 18 (1997) 1099.

Koch, O. G. and Koch-Dedic, G. A., Siliconmolybdänblau-Verfahren, in Handbuch der Spurenanalyse, Springer-Verlag, Berlin, (1974) 1105.

Kortesuo, P., Ahola, M. m Karslon, S., Kangasniemi, I., Kiesvaara, J., and Yli-Urpo, A., *Biomaterials*, in press.

Kortesuo, P., Ahola, M., Karlson, S., Kangasniemi, I., Kiesvaara, J., and Yli-Urpo, A., *J. Biomed. Mater. Res.*, 44 (1999) 162.

Korzeniewski, C. and Callewaert, D., M. *J. Immunol. Meth.* 64 (1983) 313–320.

Park, K. D., Piao, A. Z., Jacobs, H., Okano, T., and Kim, S. W., *Journal of Polymer Science: Part A: Polymer Chemistry*, 29 (1991) 1725.

Pitt C. G., Gratzel, M. M., Jeffcoat, A. R., Zweidinger, R., and Schindler, A., *J. Pharm. Sci.*, 68 (1979) 1534.

Smith, P. K., Mallia, S., and Hermanson, G. T., *Analytical Biochemistry*, 109 (1980) 466.

Södergård, A., *J. Polym. Sci. part A: Poly. Chem.*, 36 (1998) 1805.

Södergård, A., *Polym. Preprints*, 2 (1998).

Ye, W.-P. and Chien, Y. W., *Pharm. Dev. Technol.*, 1 (1996) 1.

The invention claimed is:

1. A device made of a material suitable for medical use in humans and/or animals, said material bearing or being capable of binding a biologically active agent, wherein said material is multilayered and formed into a body of the shape of a finished device comprising
   a) a core material, wherein said core material is formed into a body, optionally into a body having the shape of a finished device,
   b) two or more layers of coating material of which the first layer has been applied onto said core material and additional layers have been applied onto said coating material of a preceding layer and
   c) at least one layer of coating material capable of binding said biologically active agent
   wherein said coating material is a biopolymer, a sol-gel produced silica gel or a biologically active molecule, and
   wherein said layers are asymmetric such that different layers cover different portions of the core material, different layers comprise different biologically active agents, or both.

2. A method for the preparation of a multilayered material for medical use in humans and/or animals bearing a biologically active agent, said material comprising
   a) a core material, wherein said core material is formed into a body, optionally into a body having the shape of a finished device,
   b) two or more layers of coating material of which the first layer has been applied onto said core material and additional layers have been applied onto said coating material of a preceding layer and
   c) said biologically active agent incorporated in at least one of the coating layers, and wherein said coating material is a biopolymer, a sol-gel produced silica gel or a biologically active molecule, comprising the repeated steps of
   i) coating said core material or a coating material of a preceding layer with a coating material which optionally can comprise a biologically active agent and ii) optionally binding a biologically active agent to said coating, wherein said layers are asymmetric such that different layers cover different portions of the core material, different layers comprise different biologically active agents, or both.

3. The method according to claim 2 wherein the core material has been formed into a body, optionally into a body having the shape of a finished device, wherein a coating is generated on the core material or a coating material of a preceding layer on a desired region of the body.

4. The method of claim 3, wherein the attachment of a coating layer is improved by using a surface modification technique on a core surface or a surface of the previous coating layer.

5. The method of claim 4, wherein said surface modification technique is radiation induced grafting or a silylation treatment.

6. The device of claim 1, wherein said biodegradable silica body is a bioactive glass or a sol-gel produced silica gel.

7. The device of claim 1, wherein said biopolymer is a polylactide or a cellulose.

8. The device of claim 1, wherein said coating material is heparin.

9. The device of claim 1, wherein a biologically active agent is composed in a sol-gel produced silica gel body or a sol-gel produced silica gel coating layer, or a biopolymer body or biopolymer coating layer.

10. The device of claim 1, wherein the core material and all coating materials are biodegradable.

11. The device of claim 1, wherein said body has a shape selected from the group consisting of a granule, a spherulite, a sheet, a film, a plate, a stick, a pin, a screw, a tube, a fiber, a hollow fiber, a woven fabric, a non-woven fabric and a shape resembling at least a portion of a human or animal body part.

12. The device of claim 1, wherein said body has a shape selected from the group consisting of a stent, a dental implant, an orthopedic implant, an implant for controlled drug delivery, a bone fixation pin, a fixation plate, and a regeneration matrix.

13. The device of claim 1, wherein the biologically active agent is a member selected from the group consisting of a polypeptide, a protein, a polysaccharide, an oligosaccharide, a mono- or disaccharide, an organic compound, an organometallic compound or an inorganic compound containing any element with an atomic number ranging from 3 to 84.

14. The device of claim 1, wherein the biologically active agent is an inorganic ion or a polymer thereof, silica gel per se, silica gel loaded with a therapeutical agent, heparin or its derivative, a growth factor, a growth factor producing virus, a growth factor inhibitor, an integrin blocker (e.g. a IIa/IIIb inhibitor), an oligonucleotide or a complete functional or partial gene in sense or antisense orientation in a suitable expression vector or any other expression vector construct for local delivery of said biologically active agent.

15. The device of claim 1, wherein said material is formed into a body having the shape of a stent, an inner wall of which is provided with a biologically active agent which is an inorganic ion or a polymer thereof, silica gel per se, silica gel loaded with a therapeutical agent, heparin, a growth factor, a growth factor producing virus, a growth factor inhibitor, an integrin blocker (e.g. a IIa/IIIb inhibitor), an oligonucleotide or a complete or partial functional gene in sense or antisense orientation in a suitable expression vector or any other expression vector construct; and which biologically active agent is released at a controlled rate in in vivo conditions.

* * * * *

UNITED STATES PATENT AND TRADEMARK OFFICE
CERTIFICATE OF CORRECTION

PATENT NO. : 6,991,802 B1  Page 1 of 1
APPLICATION NO. : 10/069785
DATED : January 31, 2006
INVENTOR(S) : Manja Ahola et al.

It is certified that error appears in the above-identified patent and that said Letters Patent is hereby corrected as shown below:

On the Title page, Item (75) Inventors, please insert the third named Inventor:
Eija SAILYNOJA, Turku (FI)

Signed and Sealed this

Eleventh Day of July, 2006

JON W. DUDAS
*Director of the United States Patent and Trademark Office*